United States Patent

Fest et al.

Patent Number: 4,931,465
Date of Patent: Jun. 5, 1990

[54] BENZALDOXIME CARBAMATE DERIVATIVES

[75] Inventors: Christa Fest, Wuppertal; Wilhelm Brandes, Leichlingen; Stefan Dutzmann, Düsseldorf; Gerd Hänssler, Leverkusen; Karl-Heinz Kuck, Langenfeld, all of Fed. Rep. of Germany

[73] Assignee: Bayer Akatiengesellschaft, Leverkusen, Fed. Rep. of Germany

[21] Appl. No.: 165,651

[22] Filed: Mar. 8, 1988

[30] Foreign Application Priority Data

Mar. 11, 1987 [DE] Fed. Rep. of Germany ....... 3707687

[51] Int. Cl.$^5$ .................... A01N 47/12; C07C 147/06
[52] U.S. Cl. .................... 514/477; 558/391; 560/12; 560/29; 560/31; 560/32; 560/115; 560/159
[58] Field of Search ........ 564/255; 514/477; 558/391; 560/12, 29, 31, 32, 115, 159

[56] References Cited

U.S. PATENT DOCUMENTS 4,716,176 12/1987 Fest et al. ................. 564/255

FOREIGN PATENT DOCUMENTS 0205076 12/1986 European Pat. Off. .......... 564/255
3520943 12/1986 Fed. Rep. of Germany .
423350 4/1967 Switzerland .

*Primary Examiner*—Bruce D. Gray
*Attorney, Agent, or Firm*—Sprung Horn Kramer & Woods

[57] ABSTRACT

Fungicidally active novel benzaldoxime carbamate derivatives of the formula

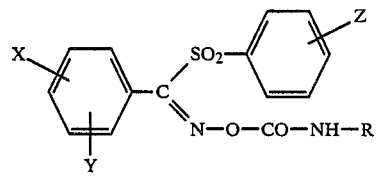

in which
X represents hydrogen or halogen,
Y represents halogen or alkyl,
Z represents hydrogen, halogen, alkyl, alkoxy or halogenoalkyl, and
R represents alkyl, halogenoalkyl, cyanoalkyl, and also phenyl or phenylalkyl, both of which are optionally monosubstituted to polysubstituted by identical or different substituents, or represents tosyl, or cycloalkyl which is optionally monosubstituted to polysubstituted by identical or different substituents, with the exception of those compounds in which X represents 2-chloro, Y represents 6-chloro and Z represents 4-methyl. Many of the benzaldoxime intermediates therefor are also new.

13 Claims, No Drawings

BENZALDOXIME CARBAMATE DERIVATIVES

The present invention relates to new benzaldoxime carbamate derivatives, a process for their preparation, and their use as pesticides, and in addition precursors, some of which are new.

A number of benzaldoximes, such as, for example, α-phenylsulphonyl-2,6-dichloro-benzaldoxime, have already been disclosed. Above all, their use in agents for combating wheat bunt is known, as is their use as plant-protection agents (cf. Swiss Patent No. 423,350).

In addition, benzaldoxime carbamate derivatives are known as fungicides (cf. U.S. Pat. No. 4,716,176).

However, their action is not always completely satisfactory under certain conditions, for example at low application rates.

New benzaldoxime carbamate derivatives of the formula (I)

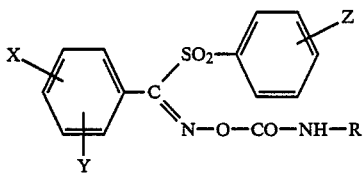

in which
X represents hydrogen or halogen,
Y represents halogen or alkyl,
Z represents hydrogen, halogen, alkyl, alkoxy or halogenoalkyl and
R represents alkyl, halogenoalkyl, cyanoalkyl, and also phenyl or phenylalkyl, both of which are optionally monosubstituted to polysubstituted by identical or different substituents, or represents tosyl, or cycloalkyl which is optionally monosubstituted to polysubstituted by identical or different substituents, apart from the compounds in which X represents 2-chloro and Y represents 6-chloro, Z represents 4-methyl and R represents the abovementioned radicals, have now been found.

It has furthermore been found that the benzaldoxime carbamate derivatives of the formula (I)

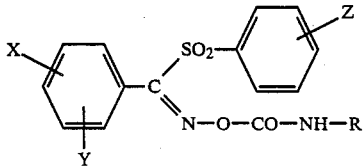

in which
X represents hydrogen or halogen,
Y represents halogen or alkyl,
Z represents hydrogen, halogen, alkyl, alkoxy or halogenoalkyl and
R represents alkyl, halogenoalkyl, cyanoalkyl, and also phenyl or phenylalkyl, both of which are monosubstituted to polysubstituted by identical or different substituents, or represents tosyl, or cycloalkyl which is optionally monosubstituted to polysubstituted by identical or different substituents,
apart from the compounds in which X represents 2-chloro, Y represents 6-chloro, Z represents 4-methyl and R represents the abovementioned radicals, are obtained when α-phenylsulphonyl-benzaldoximes of the formula (II)

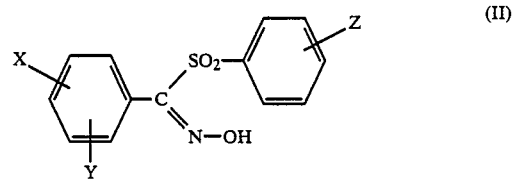

are reacted with isocyanates of the formula (III)

in which X, Y, Z and R have the abovementioned meanings, if appropriate, in the presence of solvents or diluents at temperatures from 0° C. to 100° C.

The benzaldoxime carbamate derivatives of the formula (I) according to the invention have strong biological properties, above all fungicidal properties.

Surprisingly, the compounds according to the invention exhibit a considerably greater activity, above all a fungicidal activity, than the compounds which are known from the prior art and which are very similar compounds structurally and/or regarding their action.

The compounds of the formula (I) according to the invention can be produced as syn- or anti-isomers or as mixtures thereof in various compositions. The invention relates both to the pure isomers and to the isomeric mixtures.

Formula (I) provides a general definition of the benzaldoxime carbamate derivatives according to the invention. Preferred compounds of the formula (I) are those in which
X represents hydrogen or halogen,
Y represents halogen, or straight-chain or branched alkyl having 1 to 4 carbon atoms,
Z represents hydrogen, halogen, in each case straight-chain or branched alkyl, alkoxy or halogenoalkyl, in each case having 1 to 4 carbon atoms and, if appropriate, 1 to 9 identical or different halogen atoms, and
R represents straight-chain or branched alkyl having 1 to 6 carbon atoms, straight-chain or branched halogenoalkyl having 1 to 10 carbon atoms and 1 to 9 identical or different halogen atoms, cyanoalkyl having 1 to 8 carbon atoms in the alkyl part, phenyl or phenylalkyl which has 1 to 4 carbon atoms in the straight-chain or branched alkyl part and each of which is optionally monosubstituted to pentasubstituted by halogen, straight-chain or branched alkyl having 1 to 6 carbon atoms, straight-chain or branched alkoxy having 1 to 4 carbon atoms, or straight-chain or branched halogenoalkyl or halogenoalkoxy in each case having 1 to 4 carbon atoms and in each case 1 to 9 identical or different halogen atoms, the substituents being identical or different, represents tosyl, or cycloalkyl having 5 to 7 carbon atoms which is optionally monosubstituted to pentasubstituted by straight-chain or branched alkyl having 1 to 4 carbon atoms, the substituents being identical or different,
apart from the compounds in which X represents 2-chloro, Y represents 6-chloro, Z represents 4-methyl and R represents the abovementioned radicals.

Particularly preferred compounds of the formula (I) are those in which

X represents hydrogen, fluorine or chlorine,

Y represents fluorine, chlorine, methyl, ethyl, n- or i-propyl,

Z represents hydrogen, fluorine, chlorine, straight-chain or branched alkyl, alkoxy or halogenoalkyl in each case having 1 to 3 carbon atoms and 1 to 5 identical or different halogen atoms, such as fluorine and chlorine, and R represents straight-chain or branched alkyl having 1 to 4 carbon atoms, such as methyl, ethyl, n-propyl, i-propyl, n-butyl, i-butyl, s-butyl and t-butyl, straight-chain or branched halogenoalkyl having 1 to 8 carbon atoms and 1 to 5 identical or different halogen atoms, such as fluorine, chlorine, bromine and iodine, for example 2-chloroethyl, 3-chloro-n-propyl, 4-chloro-n-butyl, 4-chloro-n-pentyl and 6-chloro-n-hexyl, cyanoalkyl having 1 to 6 carbon atoms in the alkyl part, for example 3- or 5-cyano-n-pentyl, phenyl which is optionally monosubstituted, disubstituted or trisubstituted by fluorine, chlorine, straight-chain or branched alkyl having 1 to 3 carbon atoms, alkoxy having 1 or 2 carbon atoms, halogenoalkyl having 1 or 2 carbon atoms and 1 to 5 identical or different halogen atoms and halogenoalkoxy having 1 or 2 carbon atoms and 1 to 5 identical or different halogen atoms, the substituents being identical or different, phenylmethyl or phenylethyl, each of which is optionally monosubstituted, disubstituted or trisubstituted by alkyl having 1 to 3 carbon atoms, represents tosyl, or cycloalkyl having 5 to 7 carbon atoms which is optionally monosubstituted, disubstituted or trisubstituted by straight-chain or branched alkyl having 1 to 3 carbon atoms, the substituents being identical or different, apart from the compounds in which X represents 2-chloro, Y represents 6-chloro, Z represents 4-methyl and R has the abovementioned meaning.

Halogen represents fluorine, chlorine, bromine or iodine, above all fluorine or chlorine, unless otherwise stated. Very particularly preferred compounds of the formula (I) are those in which X represents hydrogen, fluorine or chlorine, Y represents fluorine, chlorine or methyl, Z represents hydrogen, fluorine, chlorine, methyl, methoxy, trichloromethyl, trifluoromethyl or dichlorofluoromethyl, and R represents methyl, ethyl, n-propyl, i-propyl, n-butyl, s-butyl, i-butyl, t-butyl, 6-chloro-n-hexyl, 5-cyano-n-pentyl, phenyl which is monosubstituted, disubstituted or trisubstituted by methyl, ethyl, n-propyl, i-propyl, methoxy, ethoxy, trifluoromethyl, trifluoromethoxy, chlorine and fluorine, the substituents being identical or different, represents benzyl, tosyl, cyclohexyl or cyclohexyl which is monosubstituted, disubstituted or trisubstituted by methyl or ethyl, the substituents being identical or different, apart from the compounds in which X represents 2-chloro, Y represents 6-chloro, Z represents 4-methyl and R represents the abovementioned radicals.

Compounds of the formula (I) which may be mentioned in particular are those in which X represents 2-chloro, 2-fluoro, 4-chloro or hydrogen, Y represents 4-chloro, 6-chloro, 6-fluoro or 4-methyl, Z represents hydrogen, 4-chloro, 4-fluoro, 3-trifluoromethyl or 4-methoxy, and R represents methyl, ethyl, n-propyl, iso-propyl, n-butyl, iso-butyl, tert.-butyl, 6-chloro-n-hexyl, 5-cyano-n-pentyl, phenyl, 4-trifluoromethoxyphenyl, 2-, 3- or 4-methyl-phenyl, 3-chloro-4-methyl-phenyl, 3-methyl-4-chlorophenyl, 3- or 4-chlorophenyl, 3,4- or 3,5-dichloro-phenyl, 3-trifluoromethylphenyl, 4-ethoxy-phenyl, 3-chloro-4-trifluoromethylphenyl or 3,6-di-iso-propyl-phenyl, benzyl, tosyl, cyclohexyl, 3,5,5-trimethyl-cyclohexyl or 4-methyl-cyclohexyl, and those in which X represents 2-fluoro, Y represents 6-fluoro, Z represents hydrogen, 4-chloro, 4-fluoro or 4-methyl, and R has the abovementioned meaning.

In addition compounds of the formula (I) in which

X represents hydrogen,

Y represents 6-chloro,

Z represents 4-methyl and

R represents methyl, ethyl, n-propyl, iso-propyl, n-butyl, iso-butyl, tert.-butyl, 6-chloro-n-hexyl, 5-cyano-n-pentyl, phenyl, 4-trifluoromethoxyphenyl, 2-, 3- or 4-methyl-phenyl, 3-chloro-4-methyl-phenyl, 3-methyl-4-chlorophenyl, 3- or 4-chlorophenyl, 3,4- or 3,5-dichloro-phenyl, 3-trifluoromethyl-phenyl, 4-ethoxy-phenyl, 3-chloro-4-trifluoromethylphenyl or 3,6-di-iso-propylphenyl, benzyl, tosyl, cyclohexyl, 3,5,5-trimethylcyclohexyl or 4-methyl-cyclohexyl.

If α-(4-methyl-phenylsulphonyl)-2-chloro-benzaldoxime and methyl isocyanate are used as starting materials, the course of the reaction of the process according to the invention may be represented by the following equation:

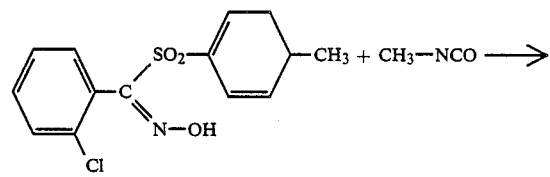

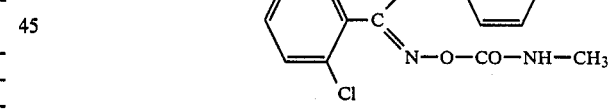

Formula (II) provides a definition of the α-phenylsulphonyl-benzaldoximes which are required as starting materials for carrying out the process according to the invention. Some of these compounds are known, as is their preparation (cf. for example, U.S. Pat. No. 3,234,255; CH 423,350; Synthesis 1974 (1), pages 49–51, and Tetrahedron 1975, 31 (6), pp. 597–600).

New and part of the invention are the compounds of the formula (IIA)

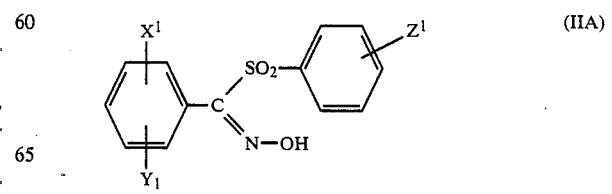

in which $X^1$ represents hydrogen, 2-fluoro or 2-chloro, $Y^1$ represents 4-chloro, 6-chloro or 6-fluoro, $Z^1$ represents 4-fluoro, 4-chloro, 3-trifluoromethyl or 4-methoxy and $Z^1$ in addition represents hydrogen or 4-methyl if at least one of the radicals $X^1$ and $Y^1$ represents fluorine.

The known and also the new compounds of the formulae (II) and (IIA) can be obtained by reacting α-halogenobenzaldoximes of the formula (IV) or (IVA)

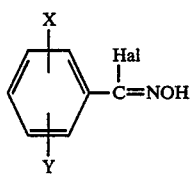
(IV)

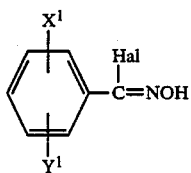
(IVA)

with phenylsulphinic acids of the formulae (V) and (VA) respectively

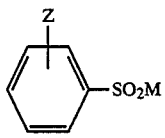
(V)

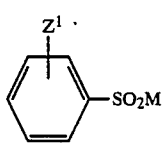
(VA)

in which

X, Y, Z, $X^1$, $Y^1$ and $Z^1$ have the abovementioned meanings,

Hal represents halogen, preferably chlorine, and

M represents hydrogen or an alkali metal equivalent, if appropriate in the presence of a solvent and if appropriate in the presence of an acid-binding agent and at temperatures from 0° C. to 60° C.

The compounds of the formulae (II) and (IIA) also exhibit a fungicidal action at appropriate application rates.

The process for the preparation of the starting compounds of the formulae (II) and (IIA) can, if appropriate, be carried out in the presence of a solvent or diluent. Suitable as such are preferably alcohols, such as methanol.

The reaction temperatures may vary within a relatively wide range. In general, the process is carried out at temperatures between 0° and 60° C., preferably between 15° and 30° C.

Formula (III) provides a general definition of the isocyanates which are furthermore required as starting materials. These isocyanates are known compounds of organic chemistry.

The process according to the invention may, if appropriate, be carried out in the presence of a solvent or diluent. Suitable as such are, in principle, all inert organic solvents. Hydrocarbons, optionally chlorinated, such as, for example, benzene, toluene, xylene, methylene chloride, chloroform, carbon tetrachloride, chlorobenzene and dichlorobenzene, are preferably used.

The reaction temperatures may vary in a relatively wide range. In general, the process is carried out at temperatures between 0° and 100° C., preferably between 15° and 50° C.

When carrying out the process according to the invention, the reactants are allowed to react with one another in approximately equimolar amounts. The reaction mixture is worked up in a conventional fashion, in particular by filtering off under suction, washing and drying the precipitated reaction product or by evaporating the reaction solution and triturating the residue with an organic solvent, such as, for example, ether.

The reaction can be initiated, if appropriate, by adding a few drops of a base, such as, for example, triethylamine.

The active compounds according to the invention have a strong biological action and can be employed in practice for combating undesired pests. The active compounds are suitable for use, for example, as pesticides, above all as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation: Xanthomonas species, such as, for example, *Xanthomonas campestris pv. oryzae;* Pseudomonas species, such as, for example, *Pseudomonas syringae pv. Lachrymans;* Erwinia species, such as, for example, *Erwinia amylovora;* Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention can be employed particularly successfully for combating fruit and vegetable diseases caused, for example, by Phytophthora infestans, Venturia species and Erwinia species, for combating rice diseases caused by *Pyricularia oryzae* and for combating cereal diseases caused, for example, by Puccinia species.

The action against cereal diseases caused, for example, by *Cochliobolus sativus, Pyrenophora teres* and *Leptophaeria nodonum*, likewise the good bactericidal invitro action and the action against hygiene and stored-product pests at appropriate application concentrations should also be mentioned. At appropriate concentrations and applications, some compounds also exhibit a herbicidal action.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, argillaceous earths, talc, chalk, quartz, attapulgite, montmorillonite or diatomaceous earth, and ground synthetic minerals, such as finely divided silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seeds, amounts of active compound of 0.001 to 50 g per kilogram of seeds, preferably 0.01 to 10 g, are generally required.

For the treatment of soil, active compound concentrations of 0.00001 to 0.1% by weight, preferably 0.0001 to 0.02% by weight, are required at the place of action.

USE EXAMPLES

In the following use examples, the compounds shown below are employed as comparison substances:

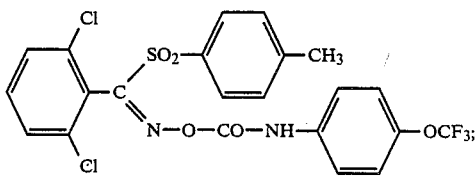

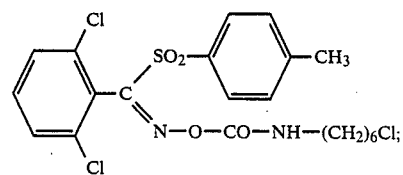

-continued $$\text{2,6-Cl}_2\text{C}_6\text{H}_3-\underset{\underset{\displaystyle N-O-CO-NHC_4H_9\text{-tert, or } -NHC_4H_9\text{-n}}{\|}}{C}-SO_2-C_6H_4-CH_3\text{-}p$$

$$\text{2,6-Cl}_2\text{C}_6\text{H}_3-\underset{\underset{\displaystyle N-O-CO-NHCH_3}{\|}}{C}-SO_2-C_6H_4-CH_3\text{-}p$$

$$\text{2,6-Cl}_2\text{C}_6\text{H}_3-\underset{\underset{\displaystyle N-O-CO-NH-SO_2-C_6H_4-OCF_3}{\|}}{C}-SO_2-C_6H_4-CH_3\text{-}p$$

$$\text{2,6-Cl}_2\text{C}_6\text{H}_3-\underset{\underset{\displaystyle N-O-CO-NHC_2H_5}{\|}}{C}-SO_2-C_6H_4-CH_3\text{-}p$$

$$\text{2,6-Cl}_2\text{C}_6\text{H}_3-\underset{\underset{\displaystyle N-O-CO-NH-C_6H_4-CF_3\text{-}m}{\|}}{C}-SO_2-C_6H_4-CH_3\text{-}p$$

(all known from U.S. Pat. No. 4,716,176).

EXAMPLE A

Pyricularia test (rice)/protective

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

The compounds according to the invention exhibit a better action compared to the prior art, for example, Preparation Examples 6, 14, 15, 16, 27, 20, 26, 28, 30, 31, 24, 19, 13 and 11.

EXAMPLE B

Venturia test (apple)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

The compounds according to Preparation Examples 4, 32, 20, 29, 31, 21, 23 and 24 are superior to those known from the prior art.

EXAMPLE C

Phytophthora test (tomato)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Phytophthora infestans.

The plants are placed in an incubation cabin at 100% relative atmospheric humidity and at about 20° C.

Evaluation is carried out 3 days after the inoculation.

In this test, the compounds according to Preparation Examples 27, 20, 29 and 23, for example, exhibit clearly superior activity compared to the prior art.

EXAMPLE D

Puccinia test (wheat) / protective /

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of Puccinia recondita in a 0.1% strength aqueous agar solution. After the spore suspension has dried on, the plants are sprayed with the preparation of active compound until dew-moist. The plants remain in an incubation cabin at 20° C. and 100% relative atmospheric humidity for 24 hours.

The plants are placed in a greenhouse at a temperature of about 20° C. and a relative atmospheric humidity of about 80% in order to promote the development of rust pustules.

The compounds according to the invention perform extremely well.

EXAMPLE E

Erwinia amylovora test/bacteriosis/apple/protective

Solvent: 49 parts by weight of acetone

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated by spraying over with an aqueous suspension of Erwinia amylovora. After an incubation period of 48 hours at 100% relative atmospheric humidity, the plants remain in a climatic chamber at 24° C. and 70–80% relative atmospheric humidity for 8 days until they are evaluated.

In this test, the compounds according to Preparation Examples 26 and 23, for example, exhibit a clearly superior activity compared to the prior art.

PREPARATION EXAMPLES

Example 1

(I)

31 g (0.1 mol) of α-(4-methyl-phenylsulphonyl)-2-chlorobenzaldoxime are dissolved in 260 ml of methylene chloride, and 5.7 g (0.1 mol) of methyl isocyanate are added at room temperature. In order to initiate the reaction, a few drops of triethylamine are added. The reaction proceeds slightly exothermically. The reaction mixture is stirred overnight at room temperature, becoming a clear solution. This solution is evaporated in vacuo, an amorphous residue remaining. This residue is triturated with ether and filtered off under suction. 19.8 g (54% of theory) of the desired substance having a melting point of 166°–169° C. are obtained.

The following compounds of the formula (I)

(I)

are prepared in an analogous fashion to Example 1:

| Ex. No. | X 2-position | Y 6-position | Z 4-position | R | Physical data (melting point °C.) |
|---|---|---|---|---|---|
| 2 | Cl | Cl | H | (2-methylphenyl) | 188 (decomp.) |
| 3 | Cl | Cl | H | (4-methylphenyl) | 189 (decomp.) |
| 4 | Cl | Cl | H | (phenyl) | 194 (decomp.) |
| 5 | Cl | Cl | F | —$C_2H_5$ | 182 |
| 6 | Cl | Cl | Cl | —$(CH_2)_6Cl$ | 118 |
| 7 | Cl | Cl | Cl | (2-methylphenyl) | 181 |
| 8 | Cl | Cl | Cl | (3-methylphenyl) | 161 |
| 9 | Cl | Cl | Cl | (4-methylphenyl) | 191 |
| 10 | F | F | H | (3,3,5-trimethylcyclohexyl) | 140 |
| 11 | F | F | H | —$C_2H_5$ | 143 |
| 12 | F | F | Cl | —$C_2H_5$ | 146 |
| 13 | F | F | Cl | (3,3,5-trimethylcyclohexyl) | 156 |
| 14 | Cl | Cl | H | —$C_2H_5$ | 184 |
| 15 | Cl | Cl | H | (3-methylphenyl) | 177 (decomp.) |

-continued

| Ex. No. | X 2-position | Y 6-position | Z 4-position | R | Physical data (melting point °C.) |
|---|---|---|---|---|---|
| 16 | Cl | Cl | H | 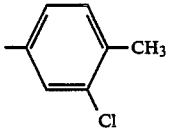 (4-CH₃, 3-Cl phenyl) | 188 |
| 17 | Cl | Cl | H | 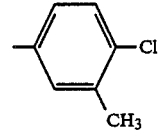 (4-Cl, 3-CH₃ phenyl) | 189 |
| 18 | Cl | F | CH₃ | 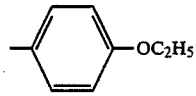 (4-OC₂H₅ phenyl) | 146 |
| 19 | F | F | CH₃ | —C₂H₅ | 153 |
| 20 | H | Cl | CH₃ | —(CH₂)₆—Cl | 83 |
| 21 | H | Cl | —CH₃ | 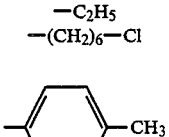 (4-CH₃ phenyl) | 182 |
| 22 | H | Cl | —CH₃ | 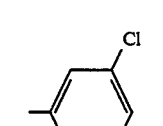 (3,5-diCl phenyl) | 182 |
| 23 | H | Cl | —CH₃ | —C₄H₉-n | 124 |
| 24 | H | Cl | —CH₃ | —C₄H₉-i | 140 |
| 25 | H | Cl | —CH₃ | 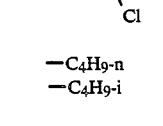 (4-Cl phenyl) | 183 |
| 26 | H | Cl | —CH₃ | —(CH₂)₅—CN | 83 |
| 27 | H | Cl | —CH₃ | —C₂H₅ | 146 |
| 28 | H | Cl | —CH₃ | 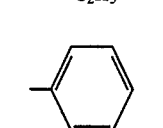 (3-Cl phenyl) | 163 |
| 29 | H | Cl | —CH₃ | 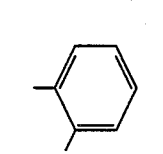 (2-CH₃ phenyl) | 141 |
| 30 | H | Cl | —CH₃ | 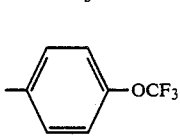 (4-OCF₃ phenyl) | 152 |
| 31 | H | Cl | —CH₃ |  (cyclohexyl) | 161 |
| 32 | H | Cl | —CH₃ |  (4-CH₃ cyclohexyl) | 174 (decomp.) |
| 33 | Cl | Cl | Cl | —C₃H₇-i | 160 |
| 34 | H | Cl | —CH₃ | 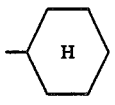 (2-CH₃ phenyl) | 134 |
| 35 | H | Cl | —CH₃ | 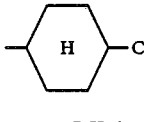 (3-CH₃ phenyl) | 163 |
| 36 | Cl | Cl | H | 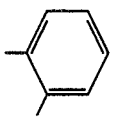 (cyclohexyl) | 192 |
| 37 | Cl | Cl | H | 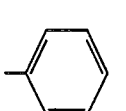 (2,6-diCl phenyl) | 195 |
| 38 | Cl | Cl | H | —CH₃ | 175 |
| 39 | Cl | Cl | H | —C₃H₇-n | 168 |
| 40 | Cl | Cl | H | —C₃H₇-i | 170 (decomp.) |
| 41 | Cl | Cl | H | —C₄H₉-n | 158 |
| 42 | Cl | Cl | H | —C₄H₉-i | 166 |
| 43 | Cl | Cl | H | —(CH₂)₅—CN | 132 |
| 44 | Cl | Cl | H | —C₄H₉-t | 162 (decomp.) |
| 45 | Cl | Cl | H | —(CH₂)₆—Cl | 121 |
| 46 | Cl | Cl | H | —CH₂— 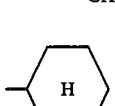 (benzyl) | 183 |
| 47 | Cl | Cl | H | 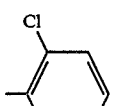 (trimethyl cyclohexyl) | 174 |
| 48 | Cl | Cl | H | 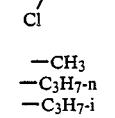 (4-CH₃ cyclohexyl) | 159 |

| Ex. No. | X 2-position | Y 6-position | Z 4-position | R | Physical data (melting point °C.) |
|---|---|---|---|---|---|
| 49 | Cl | Cl | H | —C₆H₄-OC₂H₅ (4-) | 148 |
| 50 | Cl | Cl | H | —C₆H₄-CF₃ (3-) | 176 (decomp.) |
| 51 | Cl | Cl | H | —C₆H₃(CF₃)(Cl) (3-Cl, 4-CF₃) | 172 |
| 52 | Cl | Cl | H | —C₆H₄-Cl (3-) | 177 (decomp.) |
| 53 | Cl | Cl | H | —C₆H₃Cl₂ (3,4-) | 187 |
| 54 | Cl | Cl | H | —C₆H₃Cl₂ (3,5-) | 183 |
| 55 | Cl | Cl | H | —C₆H₄-Cl (4-) | 196 |
| 56 | Cl | F | CH₃ | —C₆H₃(Cl)(CH₃) (3-CH₃, 4-Cl) | — |
| 57 | Cl | Cl | Cl | —C₆H₃Cl₂ (2,6-) | 175 |
| 58 | Cl | Cl | Cl | —C₆H₄-OC₂H₅ (4-) | 164 |
| 59 | Cl | Cl | Cl | —C₆H₃(Cl)(CH₃) (3-CH₃, 4-Cl) | 188 (decomp.) |
| 60 | Cl | Cl | Cl | cyclohexyl | 175 |
| 61 | Cl | Cl | Cl | phenyl | 159 (decomp.) |
| 62 | Cl | Cl | Cl | —CH₃ | 185 |
| 63 | Cl | Cl | Cl | —C₂H₅ | 158 |
| 64 | Cl | Cl | Cl | —C₃H₇-n | 172 |
| 65 | Cl | Cl | Cl | —C₄H₉-n | 153 |
| 66 | Cl | Cl | Cl | —C₄H₉-i | 174 |
| 67 | Cl | Cl | Cl | —C₄H₉-t | 168 (decomp.) |
| 68 | Cl | Cl | Cl | —(CH₂)₅—CN | 151 (decomp.) |
| 69 | Cl | Cl | Cl | —CH₂—C₆H₅ | 180 |
| 70 | Cl | Cl | Cl | 3,3,5-trimethylcyclohexyl | 175 |
| 71 | Cl | Cl | Cl | 4-methylcyclohexyl | 170 |
| 72 | Cl | Cl | Cl | —C₆H₄-CF₃ (3-) | 181 |
| 73 | Cl | Cl | Cl | —C₆H₃(CF₃)(Cl) (3-Cl, 4-CF₃) | 164 |
| 74 | Cl | Cl | F | 3,3,5-trimethylcyclohexyl | 178 |
| 75 | H | Cl | —CH₃ | —C₃H₇-n | 121 |

-continued

| Ex. No. | X 2-position | Y 6-position | Z 4-position | R | Physical data (melting point °C.) |
|---|---|---|---|---|---|
| 76 | Cl | Cl | —OCH₃ | 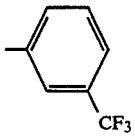 | 187 |
| 77 | F | F | —CH₃ | 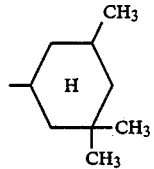 | 147 |
| 78 | H | Cl | —CH₃ | 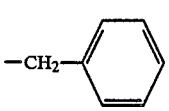 | 153 |
| 79 | Cl | Cl | Cl | 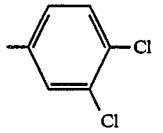 | 179 |
| 80 | H | Cl | CH₃ | 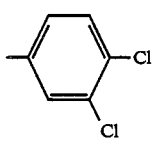 | 181 |
| 81 | Cl | Cl | Cl | 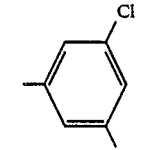 | 190 |
| 82 | F | F | —CH₃ | 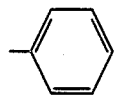 | 142 |
| 83 | H | Cl | —CH₃ | 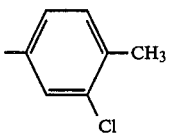 | 181 |
| 84 | H | Cl | —CH₃ | 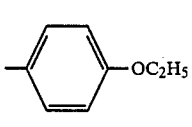 | 159 |
| 85 | H | Cl | —CH₃ | 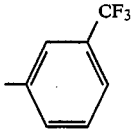 | 165 |
| 86 | Cl | Cl | H | Tosyl | 125 |

-continued

| Ex. No. | X 2-position | Y 6-position | Z 4-position | R | Physical data (melting point °C.) |
|---|---|---|---|---|---|
| 87 | H | Cl | —CH₃ | Tosyl | 65 |
| 88 | Cl | F | —CH₃ | C₂H₅ | 168 |
| 89 | Cl | F | —CH₃ | 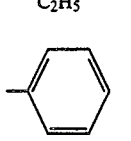 | 179 (decomp.) |
| 90 | Cl | F | —CH₃ | 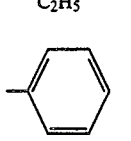 | 154 |
| 91 | Cl | F | —CH₃ | 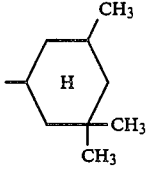 | 205 |
| 92 | Cl | F | —CH₃ | 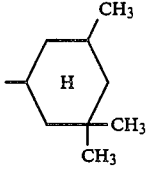 | 176 |
| 93 | Cl | F | —CH₃ | —CH₃ | 149 |
| 94 | Cl | F | —CH₃ | —C₃H₇-n | 157 |
| 95 | Cl | F | —CH₃ | —C₃H₇-i | 178 |
| 96 | Cl | F | —CH₃ | 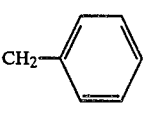 | 169 |
| 97 | Cl | F | —CH₃ | 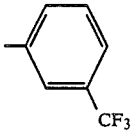 | 180 |
| 98 | Cl | F | —CH₃ | 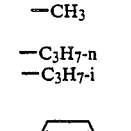 | |
| 99 | Cl | F | —CH₃ | 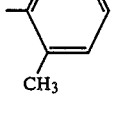 | 198 |
| 100 | F | F | —CH₃ | —CH₃ | 146 |
| 101 | F | F | —CH₃ | —C₃H₇-n | 132 |
| 102 | Cl | Cl | Cl | 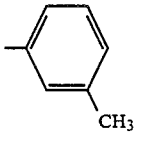 | 161 |

-continued

| Ex. No. | X 2-position | Y 6-position | Z 4-position | R | Physical data (melting point °C.) |
|---|---|---|---|---|---|
| 103 | H | Cl | H | —CH$_3$ | 98 |
| 104 | H | Cl | H | —C$_2$H$_5$ | 104 |
| 105 | H | Cl | H | —C$_3$H$_7$-n | 83 |
| 106 | H | Cl | H | —C$_3$H$_7$-i | 125 |
| 107 | H | Cl | H | —C$_4$H$_9$-i | 130 |
| 108 | H | Cl | H | —C$_4$H$_9$-sec. | 105 |
| 109 | H | Cl | Cl | —CH$_3$ | 125 |
| 110 | H | Cl | Cl | —C$_3$H$_7$-n | 75 |
| 110 | H | Cl | Cl | —C$_4$H$_9$-sec. | 104 |
| 112 | H | Cl | Cl | —C$_4$H$_9$-n | 109 |
| 113 | H | Cl | Cl | 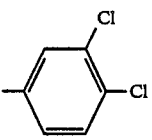 | 174 |
| 114 | H | Cl | Cl | 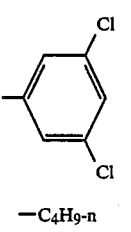 | 178 |
| 115 | H | Cl | H | —C$_4$H$_9$-n | 102 |
| 116 | H | Cl | H | 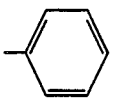 | 117 |
| 117 | Cl | F | Cl | —CH$_3$ | 131 |
| 118 | Cl | F | Cl | —CH$_5$ | 130 |
| 119 | Cl | F | Cl | —C$_3$H$_7$-n | 114 |
| 120 | Cl | F | Cl | —C$_3$H$_7$-i | 162 |
| 121 | Cl | F | Cl | —C$_4$H$_9$-n | 117 |
| 122 | Cl | F | Cl | —C$_4$H$_9$-sec. | 148 |
| 123 | H | Cl | H | 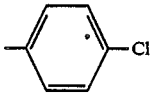 | 105 |
| 124 | H | Cl | H | 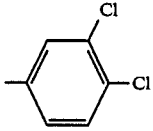 | 161 |
| 125 | H | Cl | H | 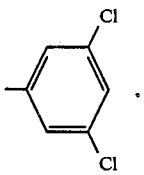 | 165 |
| 126 | H | Cl | H | 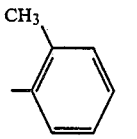 | 141 |
| 127 | H | Cl | H | 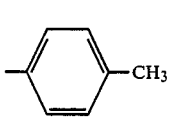 | 168 |
| 128 | Cl | F | Cl | —C$_4$H$_9$-i | 138 |
| 129 | Cl | F | Cl | —(CH$_2$)$_6$Cl | 67 |
| 130 | Cl | F | Cl | —(CH$_2$)$_5$—CN | 121 |
| 131 | H | Cl | Cl | 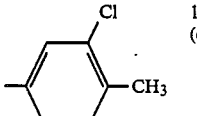 | 157 (decomp.) |
| 132 | H | Cl | Cl | 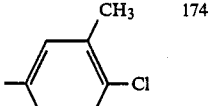 | 174 |
| 133 | H | Cl | Cl | 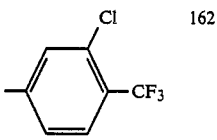 | 162 |
| 134 | H | Cl | Cl | 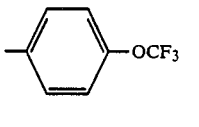 | 81 |
| 135 | H | Cl | Cl | 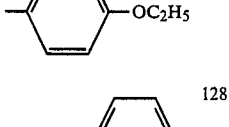 | 128 |
| 136 | H | Cl | Cl | 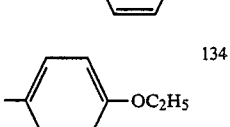 | 128 |
| 137 | H | Cl | H | 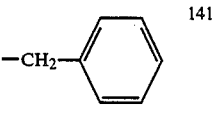 | 134 |
| 138 | H | Cl | H | 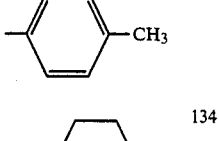 | 141 |
| 139 | H | Cl | H | 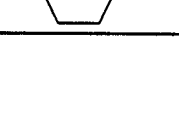 | 154 |
| 140 | H | Cl | Cl |  | 134 |

Preparation example for compounds of the formulae (II) or (IIA)

Example 1A

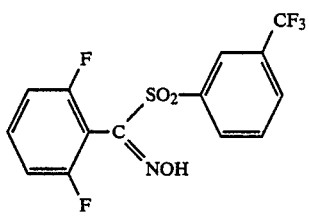

19.2 g (0.1 mol) of α-chloro-2,6-difluoro-benzaldoxime are dissolved in 200 ml of methanol, and 23.2 g (0.1 mol) of the sodium salt of 3-trifluoromethylbenzene=-sulphinic acid are added at room temperature. The reaction mixture is kept at this temperature for about 15 hours, subsequently poured into 1 liter of ice-water and washed by stirring, and the solid product is filtered off under suction, washed and dried. The reaction product is recrystallized from toluene. 24 g (62.5% of theory) of α-3-trifluoromethylphenylsulphonyl-2,6-difluorobenzaldoxime of melting point 127° C. are obtained.

Compounds of the formula (II) can be prepared analogously:

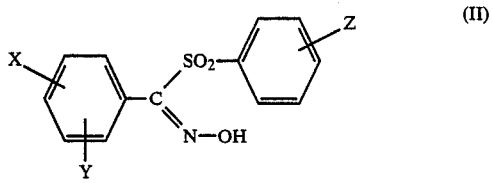

| Ex. No. | X | Y | Z | Physical data (melting point °C.) |
|---|---|---|---|---|
| 2 A | 4-Cl | 6-Cl | 4-CH₃ | 143 |
| 3 A | 2-Cl | 6-F | 4-Cl | 158 |
| 4 A | 2-Cl | 6-F | 4-CH₃ | 170 |
| 5 A | 2-Cl | 6-F | H | 143 |
| 6 A | 2-Cl | 6-F | 4-OCH₃ | 145 |
| 7 A | 6-H | 2-Cl | 4-CH₃ | 147 |
| 8 A | 2-Cl | 6-Cl | 4-H | 148 |
| 9 A | 2-Cl | 6-Cl | 4-F | 154 |
| 10 A | 2-Cl | 6-Cl | 4-Cl | 111 |
| 11 A | 2-F | 6-F | 4-H | 149 |
| 12 A | 2-F | 6-F | 4-Cl | 171 |
| 13 A | 2-F | 6-F | 4-CH₃ | 166 |
| 14 A | 2-Cl | 6-Cl | 4-OCH₃ | 163 |
| 15 A | 2-F | 6-F | 4-OCH₃ | 145 |
| 16 A | 6-H | 2-Cl | 4-OCH₃ | 141 |
| 17 A | 2-Cl | 6-Cl | 3-CF₃ | 148 |
| 18 A | 2-F | 6-F | 4-F | 148 |
| 19 A | H | 4-Cl | 4-CH₃ | 145 |
| 20 A | H | 2-Cl | H | 141 |
| 21 A | H | 2-Cl | 4-Cl | 150 |
| 22 A | 2-Cl | 6-F | 4-Cl | 158 |

It will be understood that the specification and examples are illustrative but not limitative of the present invention and that other embodiments within the spirit and scope of the invention will suggest themselves to those skilled in the art.

We claim:

1. A benzaldoxime carbamate derivative of the formula

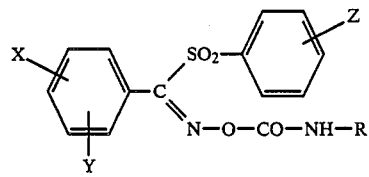

in which
X represents hydrogen, and
Y represents chlorine, or
X and Y represent fluorine,
Z represents hydrogen, halogen, alkyl, alkoxy or halogenoalkyl, and
R represents alkyl, halogenoalkyl, cyanoalkyl, and also phenyl or phenylalkyl, both of which are optionally monosubstituted to polysubstituted by identical or different substituents selected from the group consisting of halogen, straight-chain or branched alkyl having 1 to 6 carbon atoms, straight-chain or branched alkoxy having 1 to 4 carbon atoms, or straight-chain or branched halogenoalkyl or halogenoalkoxy in each case having 1 to 4 carbon atoms and in each case 1 to 9 identical or different halogen atoms, or represents tosyl, or cycloalkyl which is optionally monosubstituted to polysubstituted by identical or different alkyl substituents.

2. A benzaldoxime carbamate derivative according to claim 1, in which
Z represents hydrogen, halogen, in each case straight-chain or branched alkyl, alkoxy or halogenoalkyl, in each case having 1 to 4 carbon atoms and, if appropriate, 1 to 9 identical or different halogen atoms, and
R represents straight-chain or branched alkyl having 1 to 6 carbon atoms, straight-chain or branched halogenoalkyl having 1 to 10 carbon atoms and 1 to 9 identical or different halogen atoms, cyanoalkyl having 1 to 8 carbon atoms in the alkyl part, phenyl or phenylalkyl which has 1 to 4 carbon atoms in the straight-chain or branched alkyl part and each of which is optionally monosubstituted to pentasubstituted by halogen, straight-chain or branched alkyl having 1 to 6 carbon atoms, straight-chain or branched alkoxy having 1 to 4 carbon atoms, or straight-chain or branched halogenoalkyl or halogenoalkoxy in each case having 1 to 4 carbon atoms and in each case 1 to 9 identical or different halogen atoms, the substituents being identical or different, represents tosyl, or cycloalkyl having 5 to 7 carbon atoms which is optionally monosubstituted to pentasubstituted by straight-chain or branched alkyl having 1 to 4 carbon atoms, the substituents being identical or different.

3. A benzaldoxime carbamate derivative according to claim 1, in which
Z represents hydrogen, fluorine, chlorine, straight-chain or branched alkyl, alkoxy or halogenoalkyl in each case having 1 to 3 carbon atoms and 1 to 5 identical or different halogen atoms, and
R represents straight-chain or branched alkyl having 1 to 4 carbon atoms, straight-chain or branched halogenoalkyl having 1 to 8 carbon atoms and 1 to 5 identical or different halogen atoms, cyanoalkyl having 1 to 6 carbon atoms in the alkyl part, phenyl which is optionally monosubstituted, disubstituted or trisubstituted by fluorine, chlorine, straight-chain or branched alkyl having 1 to 3 carbon atoms, alkoxy having 1 or 2 carbon atoms, halogenoalkyl having 1 or 2 carbon atoms and 1 to 5 identical or different halogen atoms and halogenoalkoxy having 1 or 2 carbon atoms and 1 to 5 identical or different halogen atoms, the substituents being identical or different, phenylmethyl or phenylethyl, each of which is optionally monosubstituted, disubstituted or trisubstituted by alkyl having 1 to 3 carbon atoms, represents tosyl, or cycloalkyl having 5 to 7 carbon atoms which is optionally monosubstituted, disubstituted or trisubstituted by straight-chain or branched alkyl having 1 to 3 carbon atoms, the substituents being identical or different.

4. A benzaldoxime carbamate derivative according to claim 1, in which

Z represents hydrogen, fluorine, chlorine, methyl, methoxy, trichloromethyl, trifluoromethyl or dichlorofluoromethyl, and R represents methyl, ethyl, n-propyl, i-propyl, n-butyl, s-butyl, i-butyl, t-butyl, 6-chloro-n-hexyl, 5-cyano-n-pentyl, phenyl which is monosubstituted, disubstituted or trisubstituted by methyl, ethyl, n-propyl, i-propyl, methoxy, ethoxy, trifluoromethyl, trifluoromethoxy, chlorine and fluorine, the substituents being identical or different, represents benzyl, tosyl, cyclohexyl or cyclohexyl which is monosubstituted, disubstituted or trisubstituted by methyl or ethyl, the substituents being identical or different.

5. A benzaldoxime carbamate derivative according to claim 1, in which

X represents hydrogen, and
Y represents 4-chloro or 6-chloro, or
X represents 2-fluoro, and
Y represents 6-fluoro,
Z represents hydrogen, 4-chloro, 4-fluoro, 3-trifluoromethyl or 4-methoxy, and
R represents methyl, ethyl, n-propyl, iso-propyl, n-butyl, iso-butyl, tert.-butyl, 6-chloro-n-hexyl, 5-cyano-n-pentyl, phenyl, 4-trifluoromethoxyphenyl, 2-, 3- or 4-methyl-phenyl, 3-chloro-4-methyl-phenyl, 3 methyl-4-chlorophenyl, 3- or 4-chlorophenyl, 3,4- or 3,5-dichloro-phenyl, 3-trifluoromethyl-phenyl, 4-ethoxy-phenyl, 3-chloro-4-trifluoromethylphenyl or 3,6-di-isopropyl-phenyl, benzyl, tosyl, cyclohexyl, 3,5,5-trimethyl-cyclohexyl or 4-methyl-cyclohexyl.

6. A compound according to claim 1, wherein such compound is

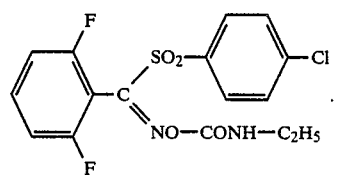

7. A compound according to claim 1, wherein such compound is

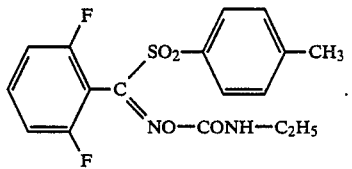

8. A compound according to claim 1, wherein such compound is

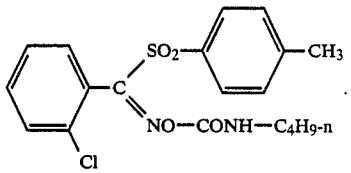

9. A compound according to claim 1, wherein such compound is

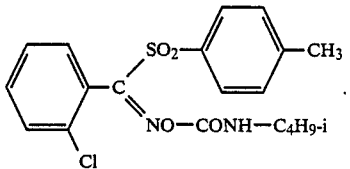

10. A compound according to claim 1, wherein such compound is

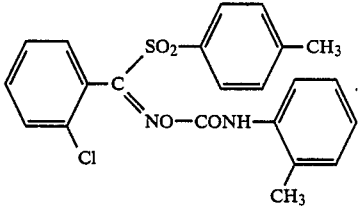

11. A compound according to claim 1, wherein such compound is

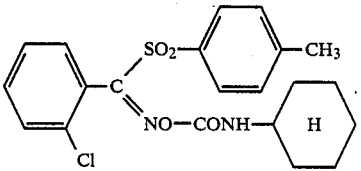

12. A fungicidal composition comprising a fungicidally effective amount of a compound according to claim 1 and a diluent.

13. A compound wherein such compound is

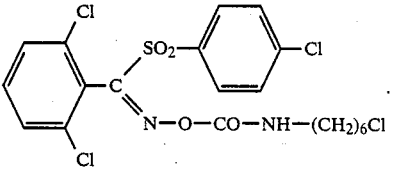

* * * * *